(12) United States Patent
Mundt et al.

(10) Patent No.: US 6,451,321 B1
(45) Date of Patent: Sep. 17, 2002

(54) IBDV STRAIN IN OVO ADMINISTRATION

(75) Inventors: Egbert Mundt, Millienhagen (DE); Adriaan Antonius Wilhelmus Maria Loon Van, Sambeek (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/878,083

(22) Filed: Jun. 8, 2001

(30) Foreign Application Priority Data

Jun. 9, 2000 (EP) ............................................. 00202042

(51) Int. Cl.$^7$ ...................... A61K 39/12; A61K 39/295; C12N 7/00; C12N 7/04
(52) U.S. Cl. ............................... 424/204.1; 424/201.1; 424/202.1; 435/235.1; 435/236
(58) Field of Search ............................ 424/204.1, 184.1, 424/205.1, 209.1, 214.1, 201.1, 202.1, 215.1; 435/235.1, 236

(56) References Cited

U.S. PATENT DOCUMENTS 5,871,748 A * 2/1999 Whitfill et al. .......... 424/215.1

FOREIGN PATENT DOCUMENTS

| EP | 0 352 835 A | 1/1990 |
|---|---|---|
| EP | 0 861 665 A | 9/1998 |

OTHER PUBLICATIONS

P. Johnston et al.: "Applications in In Ovo Technology", Poultry Science, vol. 76, No. 1, 1997, pp. 165–178.

M. Gagic et al.: "In Ovo Vaccination of Specific Pathogen Free Chickens with Vaccines Containing Multiple Agents", Avian Diseases, vol. 43, No. 2, 1999, pp. 293–301.

S. Jeurissen et al.: "The Working Mechanism of An Immune Complex Vaccine That Protects Chickens Against Infectious Bursal Disease", Immunology, vol. 95, No. 3, 1998, pp. 494–500.

J. Giambrone et al.: "Safety of Three Intermediate IBDV Vaccines Administered In Ovo", Poultry Science, vol. 78, No. suppl. 1, 1999, pp. 18–19.

* cited by examiner

Primary Examiner—Mary E. Mosher
Assistant Examiner—Myron G. Hill
(74) Attorney, Agent, or Firm—William P. Ramey, III; William M. Blackstone

(57) ABSTRACT

The present invention provides a novel infectious bursal disease virus, strain 689 which is suited as vaccine candidate for in ovo vaccination and is deposited at the European Collection of Cell Cultures, Salisbury, Wiltshine, United Kingdom under No. V00012609.

10 Claims, No Drawings

IBDV STRAIN IN OVO ADMINISTRATION

The present invention is concerned with a virus of an infectious bursal disease virus (IBDV) strain, a vaccine against infectious bursal disease (IBD), a method for the preparation of the virus, a method for the preparation of a vaccine and the use of the virus for the manufacture of a vaccine.

Infectious bursal disease virus (IBDV), a member of the birnaviridae family, is endemic in many poultry producing areas. For IBDV, two serotypes exist, serotype 1 and 2. The two serotypes may be differentiated by virus neutralisation (VN) test. Furthermore, subtypes of serotype 1 have been isolated. These so called "variant" viruses of serotype 1 can be identified by cross-neutralisation test (P. D. Lukert and Y. M. Saif, Diseases of Poultry, $9^{th}$ edition, Wolfe Publishing Ltd., Chapter 28, 648–663, 1991) a panel of monoclonal antibodies (Snyder, D. B. et al, Arch. Virol.127, 89–101, 1992) or RT-PCT (Jackwood, D. J. Proceedings of the International Symposium on Infectious Bursal Disease and Chicken Anaemia, Rauischholzhausen, Germany, 155–161, 1994). Some of these subtypes of serotype 1 of IBDV have been described in literature for example: Classical, Variant-E, GLS, RS593 and DS326 strains (Van Loon et al, Proceedings of the International Symposium on Infectious Bursal Disease and Chicken Infectious Anaemia, Rauischholzhausen, Germany, 179–187, 1994).

IBDV causes infectious bursal disease (IBD) also called Gumboro disease, an acute, highly contagious disease in chickens that has lymphoid tissue as its primary target with a selective tropism for cells of the bursa of Fabricius. The morbidity rate in susceptible flocks is high with rapid weight loss and moderate mortality. Chickens that recover from the disease may have immune deficiencies because of the destruction of the bursa of Fabricius, which is essential to the defence mechanism of the chicken. The IBDV causes severe immunosuppression in chickens younger than 3 weeks of age and induces bursal lesions in chicken up to 3 months old.

For many years the disease could be prevented by inducing high levels of antibodies in breeder flocks by the application of an inactivated vaccine, to chickens that had been primed with attenuated live IBDV vaccine. This has kept economic losses caused by IBD to a minimum. Maternal antibodies in chickens derived from vaccinated breeders prevent early infection with IBDV and diminish problems associated with immunosuppression. In addition, attenuated live vaccines have also been used successfully in commercial chicken flocks after maternal antibodies had declined.

Recently, very virulent strains of IBDV have caused outbreaks of disease with high mortality in Europe. The current vaccination program failed to protect chickens sufficiently.

Live classical IBDV vaccines are usually administered to hatched chickens through drinking water, aerosol (coarse spray) or intra-ocular (eye drops). These methods of post-hatch administration have some disadvantages, most importantly they are expensive because of the labour needed for their administration in particular in large broiler flocks.

The use of vaccines as embryo vaccines (so called in ovo vaccines) has been suggested previously (Sharma et al; Avian diseases 29, 1155–1169, 1985).

Embryo vaccination (in ovo vaccination) in principle could be advantageous due to the early age of resistance to the specific disease and the administration of a uniform dose of vaccine, into each egg using semiautomatic machines with multiple injection heads.

Usually conventional vaccines for post-hatch vaccination of birds can not be used for in ovo vaccination. Late stage embryos are highly susceptible to infection with most vaccine viruses examined including those vaccine viruses, which can be safely used in hatched chicken. As it is shown in Example 1 the commercially available IBDV vaccines for intra-ocular, coarse spray and drinking water administration in hatched chicken are not suitable for administration in ovo.

An IBDV vaccine, for in ovo administration was made available as, so called "complex vaccine". This vaccine is composed of a mixture of an live IBD virus and chicken serum containing a viral neutralising factor (VNF) in order to decrease the pathogenicity of the live virus. (Whifill et al: Proceedings of XIX World's Poultry Congress, Amsterdam, The Netherlands, 453–455, 1992). Other IBDV complex vaccines are commercially available under the trademark Bursaplex® (Embrex Inc.) and Bursamune® (Fort Dodge).

The commercially available complex vaccines have the disadvantage of using a high virulent pathogenic IBDV strain (so called hot strain) which reduces the hatchability of the vaccinated eggs, if used alone and not complexed to a serum containing a virus neutralising factor. The addition of such chicken serum to the live IBD virus strain however, results in higher manufacturing costs for the IBDV vaccine compared to those containing live IBDV strains alone.

The safety and efficacy of a live IBDV complex vaccine and of a live IBDV vaccine was tested after in ovo administration by Jungbäck et al; (Abstracts of XI International Congress of the World Veterinary Poultry Association, Budapest Hungary, 191ff, 1997). The results show, that the efficacy requirements of the European Pharmacopoea were not fulfilled by the tested vaccines after in ovo administration, because more than 10% of the in ovo vaccinated chicken showed strain severe lesions of the bursa of Fabricius after challenge with a pathogenic IBDV strain.

It is therefore the aim of the current invention to provide a safe and efficacious mild strain of IBDV that can be administered in ovo, in the absence of a serum containing virus neutralising factor, without having a negative impact on hatchability of the vaccinated egg and furthermore, to provide a cost effective manufacturing process for a vaccine for protection against IBD.

The present invention provides a virus of an IBDV strain designated as strain 689, a sample of which is deposited at the European Collection of Cell Culture, (ECACC) of Salisbury, Wiltshire, SP4 OJG, United Kingdom under accession No.V00012609. The IBD virus strain 689 according to the invention is distinct from the existing IBDV (vaccine) strains, is safe for in ovo administration, and is able to induce a solid immune response in chickens.

A virus of the IBDV strain 689 refers to viruses derived from a virus as deposited, as well as those progeny viruses derived from a virus as deposited, and obtainable for example, by serial passaging e.g. in embryonated eggs or in cell culture.

IBDV strain 689 was isolated from a chicken bursa of Fabricius from the field showing mild signs of IBDV. The bursa of Fabricius was homogenised and put on chicken embryo fibroblast cells (CEF). After 5 days of incubation a cythopathogen effect (CPE) was visible and characterised as IBDV with poly- and monoclonal antibodies. A second passage was conducted on CEF and this material (passage level 2) was used in Example 3. The IBDV strain 689 was further plaque purified 3 times and a pre seed was prepared followed by a master seed (passage level 7). The master seed virus was used in the Example 2.

The IBDV strain 689 was identified by means of ELISA using monoclonal antibodies (Moab) according to Van Loon et al (Van Loon, A. A. W. M., D. Lütticken and D. B. Snyder. Rapid quantification of infectious bursal disease (IBD) challenge, field or vaccine virus strains. International symposium on infectious bursal disease and chicken infectious anaemia, Rauischholzhausen, Germany, 179–187, 1994).

As can be seen from Example 4, the IBDV strain 689 belongs together with the commercially available IBDV vaccine strain Nobilis Gumboro strain D78 (Intervet International, Boxmeer, The Netherlands) to the classical type of IBDV, because both strains have an identical reaction pattern with the different monoclonal antibodies and are both able to replicate on primary CEF inducing a CPE.

The Examples 2 and 3 show that IBDV strain 689 is able to induce a protective immune response to a challenge with virulent classical IBDV and variant-E IBDV without causing severe lesions in the bursa of Fabricius.

The virus according to the invention is provided in a live and inactivated form, preferably in a live form.

Another aspect of the invention is a vaccine against IBD, characterised in that it comprises a virus as defined above and a pharmaceutically acceptable carrier or diluent and a method for the preparation of the vaccine.

The vaccine containing the live virus can be prepared and marketed in a form of a suspension or in a lyophilised form and additionally contains a pharmaceutically acceptable carrier or diluent customary for such compositions. Carriers include stabilisers, preservatives and buffers. Suitable stabilisers are, for example SPGA carbohydrates (such as sorbitol, mannitol, starch, sucrose, dextran, glutamate or glucose), proteins (such as dried milk serum, albumin, or casein) or degradation products thereof. Suitable buffers are for example alkali metal phosphates. Suitable preservatives are thimerosal, merthiolate and gentamicin. Diluents include water, aqueous buffer (such as buffered saline) and polyols (such as glycerol). If desired the live vaccine according to the invention may contain an adjuvant. Examples of suitable compounds and compositions with adjuvant activity are the same as mentioned below.

In another aspect of the present invention a vaccine is provided comprising the IBDV strain 689 in an inactivated form. The major advantage of an inactivated vaccine is the high level of protective antibodies of long duration that can be achieved. A vaccine containing the inactivated IBDV virus can, for example comprise one or more of the, above mentioned pharmaceutically acceptable carriers or diluents suited for this purpose. Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol® or Marcol® or a vegetable oil such as vitamin E acetate and saponins.

The vaccine according to the present invention can be administered to birds by any suitable means. Exemplary means for post hatch administration are the oral administration (e.g. in feed or drinking water), administration via parenteral routes e.g. by intramuscular injection or via eye drop forms or spray vaccination (aerosol). Inactivated vaccines are usually administered parenterally, e.g. intramuscularly or subcutaneously.

The vaccine according to the invention can also be administered in ovo, as described in U.S. Pat. No. 4,458,630. The in ovo administration of the vaccine is most preferred.

The in ovo administration of the vaccine involves the administration of the vaccine to an avian embryo while contained in the egg. The vaccine may be administered to any suitable compartment of the egg (e.g. allantois fluid, yolk sac, amnion, air cell or into the embryo) as described in the art (Sharma; Am. J. Vet. Res. 45, 1619–1623, 1984). Preferably the vaccine is administered below the shell (aircell) membrane and chorioallantoic membrane. Usually the vaccine is injected into embryonated eggs during late stages of the embryonation, generally during the final quarter of the incubation period (day 15–21), more preferably the eggs are treated between the 15.–19. day of incubation and most preferably at day 18 of the incubation period.

The mechanism of injection of the incubated eggs is not particularly critical provided that it does not unduly damage tissue and organs of the embryo or the extra-embryonic membranes surrounding it so that the treatment will not decrease hatchability or causes infection. The vaccine may be administered to the egg by any means, which transports the compound through the shell. The preferred method of administration is, however, by injection. Depending on the precise stage of development and position of the embryo the needle with a defined length will terminate in different parts of the egg. For example, a small hole is pierced with a needle 1½ inch, about 22 gauge) attached to a syringe in the shell of the large end of the egg and the vaccine is injected below the inner shell membrane and the chorioallantoic membrane. A pilot hole may be punched or drilled through the shell prior to insertion of the needle to prevent damaging or dulling of the needle. In addition if desired, the egg can be sealed e.g. by a sealing apparatus with substantially bacteria-impermeable sealing material such as wax or the like to prevent subsequent entry of undesirable bacteria.

Subsequently, the vaccinated embryonated eggs are transferred to an incubator to hatch (U.S. Pat. No. 4,458,630, WO 98/56413 and WO 95/35121). Preferably, the whole embryo vaccination process is carried out using high-speed automated vaccination systems, such as the commercially available INOVOJECT®. Such devices are also disclosed in U.S. Pat. Nos. 4,681,063 and 4,903,635, 4,040,388, 4,469,047 and 4,593,646.

The vaccine according to the invention comprises an effective dosage of the IBDV 689 virus as the active component, i.e. an amount of immunising IBDV material that will induce immunity in the vaccinated birds against challenge by a virulent IBDV virus. Immunity is defined herein, as the induction of a significant higher level of protection in a population of birds, after vaccination, compared to an unvaccinated group.

Depending on the inoculum administered, the site and manner of administration, the species, age and condition of the subject, the virus dose will range from $10^1$–$10^6$ TCID$_{50}$ (i.e. one Tissue Culture Infectious Dose 50 is the dose at which 50% of the infected tissue cultures show CPE), more preferably in a dose of $10^2$–$10^5$ TCID$_{50}$.

Another aspect of the invention is a vaccine as described above, characterised in that the vaccine additionally comprises an embryo-safe vaccine strain of another avian pathogen.

The combined administration of more than one vaccine strain is advantageous for economical reasons, because it requires fewer vaccine inoculations in the egg. Moreover, the fewer an inoculum is introduced into an egg, the less the risk of contaminating the eggs exist.

With an embryo safe vaccine strain is meant a live vaccine strain which, if inoculated into SPF eggs at incubation day 18, results in the hatchability of the eggs of at least 70%, preferably at least 80%.

Preferably, the combination vaccine additionally comprises one or more embryo-safe vaccine strains of Mareks disease virus (MDV) infectious bronchitis virus (IBV), Newcastle disease (NDV), egg drop syndrome (EDS) virus, turkey rhinotracheitis virus (TRTV) or reovirus.

Although the IBDV vaccine according to the present invention may be used effectively in chickens, also other poultry as turkeys, guinea fowl and partridges may be successfully vaccinated with the vaccine. Chickens include broilers, reproduction stock and laying stock.

Another aspect of the invention is a method for the preparation of the as disclosed above, characterised in that the virus is cultured on a suitable substrate and harvested from the substrate. IBD virus of the 689 strain according to the invention can be obtained by conventional methods known in the art.

Briefly, a susceptible substrate is inoculated with IBDV strain 689 and propagated until the virus replicated to a desired titre after which IBDV containing material is harvested. Every substrate which is able to support the replication of IBDV virus can be used in the present invention, including embryonated chicken eggs, primary (avian) cell cultures, such as embryo fibroblast cells (CEF) or chicken kidney cells (CK), or mammalian cell lines such as VERO cell line or baby hamster kidney (BHK) cell lines.

Preferably the IBDV strain 689 is propagated in primary chicken embryo fibroblasts (CEF).

More in particular, primary chicken embryo fibroblasts (CEF) cells can be prepared at a final concentration of $2 \times 10^6$ ml. The cells are cultured in Eagles minimum essential medium containing 5% foetal calf serum. To 15 ml of this cell suspension 0.1 ml IBDV strain 689, obtained from a plaque—purified clone, which was dissolved in 1 ml, can be added. After incubation for 3–6 days in a high humidity incubator at 37° C., the virus can be harvested.

Another aspect of the invention is the use of the virus according to the invention, for the manufacture of a vaccine for the protection of birds against IBD for in ovo administration.

EXAMPLE 1

Efficacy and Safety of Commercially Available IBDV Vaccine Strains for in Ovo Administration In these studies safety and efficacy of the commercially available IBDV vaccine strains Nobilis Gumboro strain D78 (Nobilis D78) and Nobilis Gumboro strain PBG98 (Nobilis PBG98) of Intervet International BV (Boxmeer, The Netherlands) for in ovo administration were investigated.
Material and Methods The commercially available vaccines were administered at day 18 of incubation at different dosages per egg. Parameters investigated were hatchability, bursa of Fabricius lesions score and the survival after challenge with the virulent classical IBDV strain F52/70.

The hatchability was investigated by calculation of the relative hatchability (hatchability of test IBDV strains compared with the hatchability of none-treated eggs). The score of the bursa of Fabricius lesions (lymphocytic depletion in the follicles) was determined after microscopically examination of the HE stained bursa: 0 (no lesions), 1 (0–20% depletion), 2 (20–40% depletion), 3 (40–60% depletion), 4 (60–80% depletion) and 5 (severe lesions, 80–100% depletion).
Results The results are summarised in Table 1.

Nobilis PBG98 has a negative influence on hatchability at the protective dose levels of >90%. At 15 days of age, the average bursal lesion score for eggs injected with a dose of 5, 6 or 7 log10TCID$_{50}$/egg of IBDV strain PBG98, was 0, 0, 0, respectively.

Nobilis D78 has a negative influence on bursal lesions. At 15 days old, the average bursal lesion score of animals vaccinated with a dose of 4.3, 5.3 or 6.3 log10 TCID50/egg of Nobilis D78 were, 3.4, 4.7 and 5.0, respectively. These results indicate that IBDV strain Nobilis D78 can induce severe (complete lymphocytic depletion) lesions in the bursa of Fabricius after in ovo vaccination.

TABLE 1

Overview of in ovo experiments with the commercial vaccine Nobilis D78 and Nobilis PBG98.

| | SPF birds | | | MDA + birds | |
|---|---|---|---|---|---|
| Strain | Dose (TCID50/ egg) | Hatch @ (%) | % Survival after challenge | Dose (TCID50/ egg) | Hatch (%) |
| D78 | 4.3 | 96 | 100 | Field | 100 |
| | 5.3 | 98 | 100 | | |
| | 6.3 | 95 | 100 | | |
| PBG98 | 2 | 98 | 50 | Field | 102 |
| | 3 | 90 | ND | | |
| | 4 | 90 | 100 | | |
| | 5 | 77 | 100 | | |
| | 6 | 82 | 100 | | |
| | 7 | 51 | 100 | | |
| PBS | | 98 | 50 | | 100 |
| — | | 100 | 20 | | |

@ - relative hatchability
PBS - phosphate buffered saline

Conclusion

The commercially available IBDV vaccine strains vaccines Nobilis Gumboro strain PBG98 and Nobilis Gumboro strain D78 are not suitable for in ovo administration. Nobilis D78 induces severe lesion in the bursa of Fabricius after in ovo administration and Nobilis PGB98 has a negative influence on hatchablity at the protective dose levels of >90%.

EXAMPLE 2

Efficacy and Safety of the IBDV 689 Strain after in Ovo Administration and Challenge with a Virulent IBDV Variant-E Strain The effect of the different vaccines is assessed by measurement of the serological response and resistance to challenge obtained from a Delaware Variant-E strain at the age of 14 days old.
Material and Methods The vaccines investigated were the IBDV strain 689 and the commercial classical IBDV vaccine Nobilis Gumboro strain D78 (Nobilis D78). The IBDV strain 689, $10^{5.3}$ TCID$_{50}$/egg, was applied via the in ovo route. Nobilis D78, $10^{3.5}$ TCID$_{50}$/egg was applied via the in ovo route.

The presence of IBDV in the bursa of Fabricius and microscopic lesions in the bursa of Fabricius of 3 animals per group were investigated and the bursa lesion score determined as described before, 3 and 17 days after vaccination and 3 and 10 days after challenge.

Efficacy: The protection against challenge obtained from a virulent IBDV strain variant-E, at the age of 14 days old was determined. The serological response against IBDV was determined with the Virus Neutralisation (VN)-test, 14 days after vaccination. A classical IBDV strain was used as VN-IBD-virus
Results Bursa of Fabricius lesions: As shown in Table 2, IBDV strain 689 does only induce mild lesions after vaccination.

Nobilis D78 induces moderate to severe lesions after vaccination. In 4 out of 12 animals (33%) vaccinated with Nobilis D78, complete lymphocytic depletion was observed 10 days after challenge. Individual data showed that animals vaccinated with both vaccines yielded complete protection against challenge.

TABLE 2

Average bursal lesion score

| Virus | Days after vaccination | | Days after challenge | |
|---|---|---|---|---|
| | 3 | 17 | 3 | 10 |
| IBDV Strain 689 | 1.7 | 1.7 | 1.0C | 0.6 |
| Nobilis D78 | 4.3 | 3.7 | 1.72C | 2.8 |
| None vaccinated controls | | | 5.0A | |

C = chronic lesions; A = acute lesions

Serological response against IBDV: It can be seen in Table 3, that IBDV strain 689 and Nobilis D78 induced good levels of antibodies against classical IBDV.

TABLE 3

Serological response 17 days after vaccination

| Virus | Classical VN virus |
|---|---|
| IBDV Strain 689 | 7.1 ± 2.2 |
| Nobilis D78 | 6.8 ± 2.4 |
| None vaccin. controls | <1.0 ± 0.0 |

VN-titre is expressed as log2 of the dilution.

Detection of IBDV antigen in the bursa of Fabricius with an ELISA systems 3 and 17 days after vaccination and three days after challenge: As shown in Table 4, the IBDV strain 689 could be detected in 2 out of 3 chickens three days after vaccination. Seventeen days after vaccination no viral antigen could be detected. No virus could be detected three days after challenge indicating that the animals were protected against challenge. Nobilis D78 virus could be isolated from all animals, three days after vaccination

TABLE 4

Presence of IBDV in the bursa of Fabricius.

| Virus | Days after vaccination | | Days after challenge | % protection* |
|---|---|---|---|---|
| | 3 | 17 | 3 | |
| IBDV strain 689 | 2/3 | 0/3 | 0/3 | 100 |
| Nobilis D78 | 3/3 | 0/3 | 0/3 | 100 |
| None vaccin. controls | | | 6/6 | 0 |

*Number of positive animals with viral antigen present per total number investigated.

Conclusions

The IBDV strain 689 is very mild after in ovo administration. In contrast, after in ovo administration of the commercial Nobilis Gumboro D78 strain some birds showed complete lymphocytic depletion even when a low dose (3.5 log10/egg) was applied. IBDV strain 689 is able to induce a serological response and complete protection against challenge with a virulent IBDV variant-E virus.

EXAMPLE 3

Efficacy and Safety of the IBDV 689 Strain after in ovo Administration and Challenge with a Classical Virulent IBDV Strain Efficacy of the IBDV strain 689 is assessed by measurement of the serological response and resistance to challenge obtained from administering the classical virulent IBDV strain F52/70 at 14 days after hatching.

Material and Methods

Eggs were divided in 4 groups of 35 eggs each. On day 18 of incubation, three groups were vaccinated with IBDV strain 689 in different dosage per egg. The negative control was injected with diluent only.

One day after hatching the bursa of Fabricius of 5 chickens per group was examined for lesions and the presence of viral antigen.

Fourteen days after hatching, serological response of all animals was investigated and the bursa of Fabricius was examined for lesions and the presence of viral antigen. For investigation of the serological response a classical IBDV strain was used as Virus Neutralisation-IBDV-virus.

All animals are challenged fourteen days after hatching with the classical virulent IBDV strain F52/70 via eye drop administration.

At three days after challenge the bursa of Fabricius of 5 chickens per group was examined for lesions and the presence of viral antigen. Ten days after challenge the bursa of Fabricius of all remaining animals was examined for microscopic lesions. The relative hatchability was investigated.

Results

Hatchability: The relative hatchabilty (hatchability compared to none-infected eggs) for eggs vaccinated with <1.3, 2.4 or 4.7 log10 TCID50/egg were: 116, 93 and 89%, respectively. The in ovo vaccination had no negative effect on hatchability.

Bursa of Fabricius lesions: As shown in Table 5, IBDV strain 689 does only induce mild lesions after vaccination. This confirms the mild nature of the IBDV strain 689. Individual data showed that all vaccinated animals were completely protected.

TABLE 5

Average bursal lesion score in the bursa of Fabricius 3 and 14 days after vaccination and 3 and 10 days after challenge

| IBDV strain 689 Dose (log10 TCID50/egg) | Days after vaccination | | Days after challenge | |
|---|---|---|---|---|
| | 3 | 17 | 3 | 10 |
| <1.3 | 0 | 1.0 | 1.0C | 0.8 |
| 2.4 | 0.8 | 1.6 | 0.8 | 1.0 |
| 4.7 | 2.2 | 1.4 | 1.8C | 2.0 |
| None vaccinated controls | 0 | 0 | 5.0A | 5.0 |

C = chronic lesions; A = acute lesions

Serological response against IBDV: As shown in Table 6, seventeen days after vaccination, all vaccinated animals averaged between 7.3 and 8.7 log2/group, which are good serological responses against classical IBDV.

TABLE 6

Serological response 17 days after vaccination

| IBDV strain 689 Dose (log10 TCID50/egg) | Classical VN virus |
|---|---|
| <1.3 | 7.3 ± 2.1 |
| 2.4 | 8.7 ± 1.4 |
| 4.7 | 8.2 ± 1.7 |
| None vaccinatedcontrols | <4.0 ± 0.0 |

VN-titre is expressed as log2 of the dilution.

Detection of IBDV antigen in the bursa of Fabricius with an ELISA systems three and seventeen days after vaccination and three days after challenge:

As shown in Table 7, three days after vaccination, vaccine virus could be isolated from 2 out of 5 and 4 out of 5 birds vaccinated with a dose of 2.4 or 4.7log10 TCID$_{50}$/egg, respectively. No vaccine virus could be detected in animals vaccinated with a dose of <1.3 log10 TCID$_{50}$/egg. No vaccine virus could be detected in any of the vaccinated animals just before challenge.

No virus could be detected in any of the vaccinated animals, three days after challenge indicating that all animals were protected against challenge. In contrast all animals in the none-vaccinated control group contained viral antigen three days after challenge.

TABLE 7

Presence of IBDV in the bursa of Fabricius.

| IBDV strain 689 Dose (log10 TCID50/egg) | Days after vaccination | | Days after challenge | |
|---|---|---|---|---|
| | 3 | 17 | 3 | % protection* |
| <1.3 | 0/5 | 0/5 | 0/5 | 100 |
| 2.4 | 2/5 | 0/5 | 0/5 | 100 |
| 4.7 | 4/5 | 0/5 | 0/5 | 100 |
| None vaccinated controls | | | 5/5 | 0 |

*Number of positive animals with viral antigen present per total number investigated.

Conclusions

IBDV Strain 689 is very mild. The IBDV-strain 689 is able to induce a serological response and complete protection against the classical virulent IBDV strain F52/70.

EXAMPLE 4

Virus Identification

Identification of IBDV strains by means of monoclonal antibody panel test

Material and Methods

Chicken embryo fibroblasts in micro titre plates were infected with different IBDV strains and are treated after incubation for three to five days at 37° C. with different monoclonal antibodies. The binding of the monoclonal antibodies to the different IBDV strains is visualised by fluorescence labelled conjugate (goat-anti-mouse).

Results

As can be seen in Table 8, IBDV strain 689 and the classical commercial vaccine strain Nobilis D78 have an identical reaction pattern with the different monoclonal antibodies (Moab).

TABLE 8

Panel pattern of different IBDV viruses with different Moab.

| Virus/Moab | B29 | 8 | R63 | BK9 | 67 | 57 | B69 |
|---|---|---|---|---|---|---|---|
| IBDV Strain 689 | + | + | + | − | − | − | + |
| Nobilis D78 | + | + | + | − | − | − | + |

TABLE 8-continued

Panel pattern of different IBDV viruses with different Moab.

| Virus/Moab | B29 | 8 | R63 | BK9 | 67 | 57 | B69 |
|---|---|---|---|---|---|---|---|
| Control IBDV strains: | | | | | | | |
| Classical | + | + | + | − | − | − | + |
| variant-E | + | + | + | + | + | − | − |
| GLS | + | + | − | − | − | + | − |

+ epitope present on virus, − epitope not present on virus.

Growth on Chicken Embryo fibroblasts (CEF): As can be seen in Table 9, IBDV strain 689 and Nobilis D78 are both able to replicate on CEF inducing a CPE.

TABLE 9

Ability to grow on CEF and inducing specific IBDV-CPE.

| Virus | CEF growth |
|---|---|
| IBDV Strain 689 | + |
| Nobilis D78 | + |

+ = does induce CPE on CEF; − = does not cause CPE on CEF.

Conclusion: IBDV strain 689 grows on CEF and belongs to the classical type of IBDV.

What is claimed is:

1. A virus which is infectious bursal disease virus strain 689, which does not cause severe lesions in the bursa of Fabricius after in ovo administration and is deposited at the European Collection of Cell Cultures, Salisbury, Wiltshire, SP4 OJG, United Kingdom under accession No. V00012609.

2. A method for the propagating of the virus according to claim 1, comprising culturing the virus on a suitable substrate and harvesting the virus from the substrate.

3. A vaccine against infectious bursal disease, comprising a virus according to claim 1 and a pharmaceutically acceptable carrier or a diluent.

4. The vaccine according to claim 3, comprising an effective dose of $10^1$–$10^6$ TCID$_{50}$, (Tissue Culture Effective Dose 50).

5. The vaccine according to claim 4, comprising a dose per egg of $10^2$–$10^5$ TCID$_{50}$.

6. The vaccine according to claim 3, which additionally comprises an embryo-safe vaccine strain of another avian pathogen.

7. A method for protecting a bird against infectious bursal disease, comprising administering an effective amount of the vaccine according to claim 3.

8. The method of claim 7, wherein the vaccine in administered to an embryo.

9. The method of claim 8, wherein the vaccine is administered in the amount of $10^1$–$10^6$ TCID$_{50}$.

10. The method of claim 9, wherein the vaccine is administered in the amount of $10^2$–$10^5$ TCID$_{50}$.

* * * * *